(12) United States Patent
Olejnik et al.

(10) Patent No.: US 10,626,446 B2
(45) Date of Patent: *Apr. 21, 2020

(54) ANALYTE ENRICHMENT METHODS AND COMPOSITIONS

(71) Applicant: QIAGEN SCIENCES, LLC, Germantown, MD (US)

(72) Inventors: Jerzy Olejnik, Brookline, MA (US); Steven Gordon, Weston, MA (US); Martina Werner, Winchester, MA (US)

(73) Assignee: QIAGEN SCIENCES, LLC, Germantown, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/178,262

(22) Filed: Nov. 1, 2018

(65) Prior Publication Data

US 2019/0292582 A1    Sep. 26, 2019

Related U.S. Application Data

(63) Continuation of application No. 14/264,758, filed on Apr. 29, 2014, now Pat. No. 10,160,995.

(60) Provisional application No. 61/822,695, filed on May 13, 2013.

(51) Int. Cl.
*C12Q 1/6806* (2018.01)
*C12Q 1/6844* (2018.01)

(52) U.S. Cl.
CPC ......... *C12Q 1/6806* (2013.01); *C12Q 1/6844* (2013.01)

(58) Field of Classification Search
None
See application file for complete search history.

(56) References Cited

U.S. PATENT DOCUMENTS

| | | | |
|---|---|---|---|
| 7,842,457 B2 | 11/2010 | Berka et al. | 435/6 |
| 8,012,690 B2 | 9/2011 | Berka et al. | 435/6.12 |
| 8,329,404 B2 | 12/2012 | McKernan et al. | 435/6.1 |
| 8,748,102 B2 | 6/2014 | Berka et al. | 435/6.12 |
| 8,765,380 B2 | 7/2014 | Berka et al. | 435/6.12 |
| 10,160,995 B2 * | 12/2018 | Olejnik | C12Q 1/6806 |
| 2006/0040297 A1 | 2/2006 | McDade et al. | 435/6 |
| 2007/0087362 A1 | 4/2007 | Church et al. | 435/6 |
| 2008/0003571 A1 | 1/2008 | McKernan et al. | 435/6 |
| 2009/0062129 A1 | 3/2009 | McKernan et al. | 506/3 |
| 2009/0191553 A1 | 7/2009 | Hendrickson | 435/6 |
| 2010/0261229 A1 | 10/2010 | Lau et al. | 435/6 |
| 2012/0270740 A1 | 10/2012 | Edwards | 506/23 |
| 2015/0275267 A1 | 10/2015 | O'Neil et al. | 435/6.11 |

OTHER PUBLICATIONS

Shendure, J. et al. (2005) "Supporting Online Material for Accurate Multiplex Polony Sequencing of an Evolved Bacterial Genome," *Science* 309(5741), 1728.
PCT International Search Report of International Application No. PCT/US2014/036591 dated Sep. 4, 2014.

\* cited by examiner

*Primary Examiner* — Angela M. Bertagna
(74) *Attorney, Agent, or Firm* — Medlen & Carroll, LLP

(57) ABSTRACT

Methods and compositions for enriching a population of particles containing an analyte are disclosed. In one embodiment, enrichment beads are used that are larger in size than the beads used for amplification. A separation device is employed that can retain larger beads with bound amplified beads. The technique finds many uses, including enriching for beads with clonally amplified template, which can be used in a variety of assays, including nucleic acid sequencing.

27 Claims, 13 Drawing Sheets

Specification includes a Sequence Listing.

| Sample | % Recovery |
|---|---|
| Control | 97.81 |
| 388 1X | 47.84 |
| 388 2X | 51.03 |
| 389 1X | 56.35 |
| 389 2X | 37.21 |
| 1288 1X | 62.73 |
| 1288 2X | 44.65 |
| 1292 1X | 48.91 |
| 1292 2X | 34.02 |

FIGURE 7

| | Stage | total counted beads | live beads | % live beads | avg intensity |
|---|---|---|---|---|---|
| Sample 1 (hybridized with Bisbiotin B2 – 46 bp) | before enrichment | 661.00 | 98.00 | 14.83 | 1756.26 |
| | spin down | 1190.00 | 33.00 | 2.77 | 1954.61 |
| | wash 1 | 557.00 | 168.00 | 30.16 | 2554.21 |
| | wash 2 | 784.00 | 420.00 | 53.57 | 2385.03 |
| | NaOH elution | 424.00 | 278.00 | 65.57 | 2639.85 |
| Sample 2 (hybridizeded with Bisbiotin B2 primer – 27 bp) | before enrichment | 593.00 | 108.00 | 18.21 | 2472.33 |
| | spin down | 1156.00 | 87.00 | 7.53 | 2522.85 |
| | wash 1 | 1786.00 | 155.00 | 8.68 | 2416.92 |
| | wash 2 | 319.00 | 84.00 | 26.33 | 2606.35 |
| | NaOH elution | 1160.00 | 715.00 | 61.64 | 2431.90 |

FIGURE 8

| Sample | Total beads | Recovery % |
|---|---|---|
| Qiacube spin | 4.67E+08 | |
| Qiacube wash | 1.55E+08 | |
| unbound | 6.22E+08 | 65.20 |
| Qiacube elute | 6.54E+07 | |
| total | 6.87E+08 | |
| Vortexer spin | 4.46E+08 | |
| Vortexer wash | 1.12E+08 | |
| unbound | 5.58E+08 | 60.52 |
| Vortexer elute | 6.07E+07 | |
| total | 6.19E+08 | |

| | Sample | % live |
|---|---|---|
| Qiacube | before enrichment | 20.51 |
| | spin | 0.84 |
| | wash | 17.56 |
| | elute | 82.98 |
| Vortexer | before enrichment | 20.67 |
| | spin | 0.76 |
| | wash | 21.62 |
| | elute | 82.92 |

FIGURE 12

| Sample | Total beads | Recovery % |
|---|---|---|
| Qiacube spin | 4.67E+08 | |
| Qiacube wash | 1.55E+08 | |
| unbound | 6.22E+08 | 65.20 |
| Qiacube elute | 6.54E+07 | |
| total | 6.87E+08 | |
| Vortexer spin | 4.46E+08 | |
| Vortexer wash | 1.12E+08 | |
| unbound | 5.58E+08 | 60.52 |
| Vortexer elute | 6.07E+07 | |
| total | 6.19E+08 | |

FIGURE 13

|  | Sample | % live |
|---|---|---|
| Qiacube | before enrichment | 20.51 |
|  | spin | 0.84 |
|  | wash | 17.56 |
|  | elute | 82.98 |
| Vortexer | before enrichment | 20.67 |
|  | spin | 0.76 |
|  | wash | 21.62 |
|  | elute | 82.92 | ns

SEQUENCE LISTING

```
<160> NUMBER OF SEQ ID NOS: 6

<210> SEQ ID NO 1
<211> LENGTH: 35
<212> TYPE: DNA
<213> ORGANISM: Artificial Sequence
<220> FEATURE:
<223> OTHER INFORMATION: Synthetic

<400> SEQUENCE: 1 ttttttttt acttcaattt actatgtagc aaagg                              35

<210> SEQ ID NO 2
<211> LENGTH: 25
<212> TYPE: DNA
<213> ORGANISM: Artificial Sequence
<220> FEATURE:
<223> OTHER INFORMATION: Synthetic

<400> SEQUENCE: 2
acttcaattt actatgtagc aaagg                                        25

<210> SEQ ID NO 3
<211> LENGTH: 25
<212> TYPE: DNA
<213> ORGANISM: Artificial Sequence
<220> FEATURE:
<223> OTHER INFORMATION: Synthetic

<400> SEQUENCE: 3
aattgttgcc cttgactgaa ttgaa                                        25

<210> SEQ ID NO 4
<211> LENGTH: 11
<212> TYPE: DNA
<213> ORGANISM: Artificial Sequence
<220> FEATURE:
<223> OTHER INFORMATION: Synthetic

<400> SEQUENCE: 4
actgaattga a                                                       11

<210> SEQ ID NO 5
<211> LENGTH: 11
<212> TYPE: DNA
<213> ORGANISM: Artificial Sequence
<220> FEATURE:
<223> OTHER INFORMATION: Synthetic

<400> SEQUENCE: 5
gcccttgact g                                                       11

<210> SEQ ID NO 6
<211> LENGTH: 11
<212> TYPE: DNA
<213> ORGANISM: Artificial Sequence
<220> FEATURE:
<223> OTHER INFORMATION: Synthetic

<400> SEQUENCE: 6
aattgttgcc c                                                       11
```

ANALYTE ENRICHMENT METHODS AND COMPOSITIONS

FIELD OF INVENTION

Methods and compositions for enriching a population of particles containing an analyte are disclosed. In one embodiment, enrichment beads are used that are larger in size than the beads used for amplification. A separation device is employed that can retain larger beads with bound amplified beads. The technique finds many uses, including enriching for beads with clonally amplified template, which can be used in a variety of assays, including nucleic acid sequencing.

BACKGROUND

Clonal amplification by the polymerase chain reaction (PCR) is well-established. A sample is partitioned so that individual nucleic acid molecules within the sample are localized within many separate regions. This can be done in a variety of ways, including isolation in microwells, capillaries, chambers and emulsions. The partitioning of the sample allows one to control the number of different molecules by limiting dilution. For example, to ensure that the instance of two nucleic acid templates in a compartment is a low frequency event, the template is diluted so that, on average, there is less than one template molecule per compartment. As a result, each compartment will generally contain "0" or "1" molecules; after PCR, amplification is either negative or positive, respectively.

One approach to clonal amplification involves solid phase amplification at limiting template dilution in aqueous compartments (i.e. droplets) in an oil emulsion, wherein the compartments contain particles (e.g. beads), template, nucleotides and nucleic acid amplification enzyme. After PCR, some compartments contain clonally amplified beads, but only at 10-20% abundance (governed by a Poisson distribution). This presents an efficiency problem. While clonal amplification is achieved, there are simply too many negative reactions. If one wants to carry out a further reaction or analysis, one cannot efficiently perform this on all of the beads, since only 10-20% would have DNA present.

What is needed is a solution to this efficiency problem.

SUMMARY OF THE INVENTION

The invention solves the low efficiency problem by selectively binding particles with DNA amplicons with enrichment beads (also called capture beads) and separating blank beads (i.e. beads lacking amplified template). One of the preferred embodiments is the use of enrichment beads that are larger in size than the beads used for amplification and a separation device that can retain larger beads with bound amplified beads, allowing unbound beads to flow through. In one embodiment, the enrichment beads are modified to comprise capture oligonucleotides (also called capture probes) or a ligand/binding partner, rendering them capable of binding only beads with DNA amplicons (also called "live" beads). After the initial separation is performed, the particles with amplicons are released from enrichment beads. For example, in one embodiment, they can be released using the same separation device (e.g. spin filter) using a release solution that breaks the interaction between the amplified bead and enrichment bead. As a result, the beads carrying amplified DNA constitute 80-100% of the total beads population and serve as much better sample for DNA sequencing or other downstream analysis. It is not intended that the process or compositions be limited to nucleic acid methods. The method and composition are generally applicable to any analyte.

In one embodiment, the present invention contemplates a method of enriching, comprising: a) providing i) an emulsion comprising one or more (and typically many) aqueous compartments in oil, at least some of said compartments comprising PCR reagents, a first primer immobilized on an emulsion bead, a second primer in solution, and template; and ii) enrichment beads, wherein said enrichment beads are different from said emulsion beads in said compartments; b) exposing said emulsion to conditions so as to amplify at least some of said template on at least some of said emulsion beads in at least some of said compartments; c) enriching for emulsion beads comprising amplified template by contacting said emulsion beads with said enrichment beads, wherein said emulsion beads comprising amplified template bind to said enrichment beads so as to make a population of emulsion bead—enrichment bead complexes and wherein emulsion beads not comprising amplified template do not bind to said enrichment beads; and d) capturing at least some of said population of complexes under conditions such that a majority of said emulsion beads not comprising amplified template are not captured. The present invention further comprises after step d): e) subjecting said population of complexes to conditions so as to separate said emulsion beads comprising amplified template from said enrichment beads such that the majority of said emulsion beads comprising amplified template separate from said enrichment beads.

It is not intended that the present invention be limited by the manner in which the enrichment beads are captured. In a preferred embodiment, the capturing in step d) comprises size selection. The present invention contemplates a variety of size selection techniques. In one embodiment, said size selection comprises density centrifugation. For example, the complexes are put on relatively dense medium (e.g. glycerol) and subjected to centrifugation. In another embodiment, said size selection comprises capturing said complexes on a filter, e.g. on the surface of a filter (or in the body of the filter) under conditions such that a majority of said emulsion beads not comprising amplified template are not captured and these uncaptured beads pass through said filter. In one embodiment, the emulsion beads pass through under the force of gravity. In one embodiment, the emulsion beads pass through under positive pressure (e.g. using a syringe). In one embodiment, a combination of forces is used (e.g. positive pressure and gravity). In one embodiment, said filter is positioned in a spin column and separation is facilitated by centrifugation.

In one embodiment, the present invention also contemplates capturing complexes on a non-filter surface. In one embodiment, the surface is modified with a ligand so that the beads are captured.

In one embodiment, the reverse primer in said emulsion is modified and carries a ligand which is then incorporated into the amplicons. The enrichment beads are coated with the binding partner that binds only the beads carrying amplicons modified with a ligand. In one embodiment such binding partner is streptavidin or avidin and the ligand is biotin.

It is not intended that the present invention be limited by the conditions that permit amplification. In one embodiment, exposing to conditions of step b) comprises temperature cycling.

As noted herein, in one embodiment the concentration of the template is controlled (e.g. by limiting dilution) such that each compartment comprises on average less than one nucleic acid template. This maximizes the frequency of amplifying only one template molecule so as to generate amplified template that is homogeneous.

In one embodiment, the present invention further contemplates breaking said emulsion after step b) and before step c). This can be done in a variety of ways (discussed below) and frees the emulsion beads from their compartments. Moreover, the oil is removed.

It is not intended that the present invention be limited by how the emulsion beads bind the enrichment beads. In one embodiment, capture oligos are on the enrichment beads. In another embodiment, a binding ligand is on the enrichment bead. With respect to the latter, in one embodiment, the present invention contemplates that said second primer comprise a first part of an interaction pair, and wherein said enrichment beads comprise the second part of said interaction pair. In one embodiment, said interaction pair is biotin and streptavidin (or avidin). In one embodiment, said second primer is biotinylated such that one strand of said amplified template terminates with a biotin, and wherein said enrichment beads comprise streptavidin and said emulsion beads comprising amplified template bind in step c) through a biotin-streptavidin interaction.

Where the enrichment beads comprise capture oligos and the emulsion beads bind the enrichment beads through hybridization (see FIG. 3), it is contemplated in one embodiment of the method, denaturing said amplified template after said breaking step and before step d). This generates single-stranded amplified template on said emulsion beads, permitting hybridization to said capture oligos on said enrichment beads. For example, said enrichment beads may comprise capture oligonucleotides comprising an at least partially complementary sequence to said amplified template, such that said emulsion beads comprising amplified template bind to said enrichment beads in step c) by hybridization.

As noted above, in one embodiment, the complexes are captured on a filter. In a preferred embodiment, said filter is a single layer nylon mesh (see FIG. 11). For further efficiency, it is contemplated in one embodiment that said mesh is positioned in a spin column. This allows for centrifuging the spin column during step d) to further the separation by facilitating passage of said unbound emulsion beads through said mesh. Alternatively, the complex can be captured on the filter and the separation can proceed by gravity. In one embodiment, the present invention contemplates the complex captured on the filter as a composition.

The capturing on the filter is done effectively where said enrichment beads are different in size from said emulsion beads. Ideally, the filter should trap the larger enrichment beads (in a complex with the emulsion beads comprising amplified template) but permit the smaller emulsion beads without amplified template to pass through the filter. It is not intended that the present invention be limited to precise size differences between the emulsion beads and enrichment beads. In one embodiment, said enrichment beads are at least five times and up to one hundred times larger than said emulsion beads. Conveniently, the enrichment beads are between 10 and 20 times larger.

It is also not intended that the complexes be limited by the number of emulsion beads involved. In a preferred embodiment, at least a portion of said enrichment beads bind more than one of said emulsion beads comprising amplified template. Indeed, typically the enrichment beads bind a plurality of emulsion beads (see FIG. 10), said emulsion beads comprising amplified template.

Once the emulsion beads are captured on the enrichment beads and the emulsion beads lacking amplified template are separated, it is useful in some embodiments to separate the captured emulsion beads from the enrichment beads. This can be done in a number of ways. In one embodiment, said emulsion beads comprising amplified template are separated from said enrichment beads by centrifugation.

It is not intended that the present invention be limited to the particular PCR reagents in the compartments of the emulsion. In one embodiment, said PCR reagents comprise nucleotides or nucleotide analogues and polymerase in a buffer.

The present invention contemplates a variety of sources of template. In one embodiment, said template comprises sheared DNA fragments (e.g. fragmented genomic DNA). In one embodiment, said sheared DNA fragments comprise 3' and 5' adaptors. In this embodiment, said first and second primers are complementary to a portion of one of said adaptors. Alternatively, primers specific for a region of the sheared DNA fragments are employed. In still another embodiment, random primers are employed.

It is not intended that the present invention be limited by the length of the primers employed. While lengths from 8 to 100 nucleotides (or more) might be employed, primers of between 20-30 nucleotides in length are conveniently employed.

During the method, separation steps can be facilitated by a variety of means. For example, in one embodiment, said emulsion beads are magnetic and said emulsion beads separated from said enrichment beads are exposed to a magnet. This can permit the convenient isolation and concentration of the separated emulsion beads.

In another embodiment, the present invention contemplates a method of enriching, comprising: a) providing i) an emulsion comprising a plurality of aqueous compartments in oil, a portion of said plurality of compartments comprising emulsion beads, PCR reagents, a forward primer immobilized on an emulsion bead, a biotinylated reverse primer in solution, and template, and ii) enrichment beads, said enrichment beads comprising streptavidin and being larger than said emulsion beads; b) exposing said emulsion to conditions so as to amplify at least some of said template on at least some of said emulsion beads in at least some of said compartments, said amplified template comprising biotin on one strand of a two strand duplex; c) breaking said emulsion so as to free said emulsion beads from said compartments; d) enriching for emulsion beads comprising amplified template among said emulsion beads free from said compartments by contacting with said enrichment beads, wherein the majority of emulsion beads comprising amplified template bind to said enrichment beads so as to make biotin-streptavidin ad complexes and the majority of emulsion beads without amplified template remain unbound; e) capturing said bead complexes on a filter under conditions such that unbound emulsion beads pass through said filter; f) subjecting said bead complexes to conditions so as to separate said emulsion beads comprising amplified template from said enrichment beads.

Again, the present invention is not limited to any particular conditions for amplification. In one embodiment, said exposing to conditions of step b) comprises temperature cycling.

As mentioned above, separations can be facilitated in a number of ways. In one embodiment, said emulsion beads in said compartments are magnetic and said magnetic beads are recovered after step c), and thereafter exposed to a magnet, and washed. This facilitates separation of the emulsion beads from the emulsion and permits multiple washing steps (if desired) to remove any residual oil and/or unreacted reagents.

The emulsion beads that are part of the complexes can be released and separated from the enrichment beads in a variety of ways. In one embodiment, said conditions of step f) comprise denaturing conditions. This separation can be facilitated in a number of ways. In one embodiment, said emulsion beads separated from said enrichment beads are magnetic. In this embodiment, said emulsion beads separated from said enrichment beads are exposed to a magnet. This permits for these emulsion beads to be readily isolated and concentrated.

It is not intended that the present invention be limited to the particular nature of type of filter. In one embodiment, said filter is a single layer nylon mesh.

For clonal amplification, the template concentration is controlled. In one embodiment, each compartment comprises on average less than one template molecule.

The capturing on the filter is enhanced where there is a difference in size between the emulsion beads and the enrichment beads. It is not intended that the present invention be limited to precise size differences. In one embodiment, said enrichment beads are at least five times and up to one hundred times larger than said emulsion beads. In one embodiment, said emulsion beads are approximately 1 μm in diameter and said enrichment beads are approximately 15 μm in diameter.

As noted above, the present invention allows for a more efficient process by recovering said separated emulsion beads comprising amplified template so as to create an enriched population contaminated with a relatively low percentage of beads without amplified template. In one embodiment, the population is contaminated with less than 20% of beads without amplified template. In one embodiment, the population is contaminated with less than 10% of beads without amplified template. In another embodiment, the population is contaminated with less than 5% of beads without amplified template. In still another embodiment, said enriched population is contaminated with less than 1% of beads without amplified template.

It is not intended that the process be limited to a small number of beads. Indeed, the present invention contemplates that many hundreds, to thousands, millions and billions of emulsion beads can be processed. In one embodiment, said enriched population comprises between 1 and 20 million beads.

As mentioned previously, for many downstream applications and assays, including sequencing, it is desired that the process generate primarily homogeneous template. In one embodiment, after the enrichment method is complete, at least 50% of said enriched population of beads comprises homogeneous template. In another embodiment, at least 80% of said enriched population of beads comprises homogeneous template. In another embodiment, between 80 and 100% comprise homogeneous template.

As mentioned previously, it is desired that the process involve a low frequency of instances wherein two different templates are amplified in a compartment of the emulsion. In one embodiment, after the enrichment method is complete, less than 30% of said enriched population of beads comprises heterogeneous template. In still another embodiment, less than 20% of said enriched population of beads comprises heterogeneous template. In yet another embodiment, less than 10% of said enriched population of beads comprises heterogeneous template. In a further embodiment, less than 1% comprise heterogeneous template.

Variations in the method are contemplated. Regardless of these variations, the present invention contemplates resulting populations of enriched particles (e.g. beads) as compositions of matter. In one embodiment, the present invention contemplates a population of beads (e.g. emulsion beads) comprising amplified template, said population contaminated with less than 20% (and more preferably 10%) of beads without amplified template, wherein at least 50% of said population comprises homogeneous template. In one embodiment, at least 80% of said population comprises homogeneous template. In still another embodiment, between 80 and 95% comprise homogeneous template. In a further embodiment, 100% comprise homogenous template.

As noted previously, the methods and compositions of the present invention solve the inefficiency problem of clonal amplification. In one embodiment, the present invention contemplates where said population is contaminated with less than 1% of beads without amplified template.

The population of enriched beads can be large in number, but small in size. For example, in one embodiment of an enriched population, said beads are 1 μm in diameter. In one embodiment of such an enriched population, said population comprises between 1 and 20 million beads. In one embodiment, said population of enriched beads are disposed in a chamber for further manipulations, including sequencing of the amplified template. In one embodiment, said population of enriched beads are disposed on a chip. In one embodiment, at least a portion of said population of enriched beads are used to make an array.

In one embodiment, the various methods and processes described above are automated. For example, the enriching method may be performed using an automated sample processing system. The system may have regions for particular tasks, e.g. centrifugation, to which and from which materials, e.g. tubes containing beads, are moved by a robotic arm or the like. The regions may have platforms, drawers, or decks. The commercially available QIAcube from Qiagen is equipped with an automated centrifuge and pipetting system which can be programmed to do all or a portion of the method steps with limited human intervention.

While not intending to be limited to any particular automated system or device, the system or device may comprise a deck, the deck comprising a plurality of sample carrier elements that may even be removably configured. The sample carriers may be both movable and removable as one piece or in pieces. The sample carriers may be positioned over a thermoblock, allowing for temperature cycling and amplification. This deck might be later removed and replaced with sample carriers positioned over a magnet, allowing for easy separation of magnetic particles, e.g. magnetic beads.

The sample processing control system may automate the sample processing system such that one or more tubes or plates (e.g. microtiter plate) may be processed according to one or more protocols. This sample processing may comprise one or more sampling protocols and steps, such as (but not limited to) adding reagents, mixing, centrifuging, removing supernatant, adding wash buffer, centrifuging again, removing supernatant, pipetting, and the like.

The automatic processing device may comprise a robotic arm having robotic movement, and in some embodiments, Cartesian movement. The arm may comprise one or more elements, such as a syringe, pipette or probe, a sensor element volume fluid and/or air applicator. The syringe, pipette or probe may be fluidically connected with a reservoir or other container, and may apply one or more of the following: rinse agents (e.g. buffers and the like), denaturing reagents (for separating DNA duplexes), additional materials (including beads). The syringe, pipette or probe may be fluidically connected to a vacuum or pump for the aspiration of reagents, such as aspiration of supernatant.

The sample processing system is configured to achieve an appropriate sequence of events that achieves a desired result to some degree. In achieving this sequence in an automated fashion to some degree the sample processing system is deemed an automated sample processing system and achieves automatic processing of at least one sample. This automated sequence as well as other aspects of the invention may be controlled by hardware, software, or some combination of them to accomplish a desired sequence with limited human intervention.

Definitions

As used herein "assay" is used broadly to mean a procedure or protocol that incorporates one or more reactions. Assays are typically used to characterize a sample of interest. An assay may be performed using at least one "assay mixture" or "reagent mixture" which is a composition from which one or more test signals are detected, before, during, and/or after processing of the composition to permit a reaction, if any, to occur. A test or assay may determine a presence (e.g., concentration) or activity, among others, of one or more analytes in a sample.

As used herein "analyte" is used broadly to mean nucleic acid, protein (e.g., an enzyme), a cell, a virus, an antibody, an organelle, a drug, a biomarker, a substance in a bodily fluid, a lipid, a carbohydrate, an inorganic substance, or any combination thereof, among others.

As used herein "reaction" is used broadly to mean a chemical reaction, a binding interaction, an enzymatic reaction, or the like. An exemplary reaction is enzyme-catalyzed polymerization. Another example is the binding of a substrate or product to a binding partner.

As used herein "reagents" are compounds or sets of compounds combined with a sample in order to perform a particular test or treatment on the sample. A reagent may be a target-specific reagent, which is any reagent composition that confers specificity for detection of a particular target or analyte in a test. A reagent optionally may include a chemical reactant and/or a binding partner for the test. In exemplary embodiments, the reagent may be an amplification reagent, such as nucleotides or nucleotide analogues. More specifically, reagents may include deoxynucleotide (and/or nucleotide) triphosphates (dNTPs and/or NTPs), and a magnesium salt in a buffer.

The sequence of a nucleic acid is defined by the order in which nucleobases are arranged along the backbone. This sequence generally determines the ability of the nucleic acid to bind specifically (hybridize or "anneal") to a partner chain (or to form an intramolecular duplex) by hydrogen bonding.

As used herein "amplification" refers to a process in which a copy number increases. Amplification may be a process in which replication occurs repeatedly over time to form multiple copies of a template. Amplification can produce an exponential or linear increase in the number of copies as amplification proceeds. Exemplary amplification strategies include polymerase chain reaction (PCR), loop-mediated isothermal amplification (LAMP), rolling circle replication (RCA), cascade-RCA, nucleic acid based amplification (NASBA), and the like. Also, amplification can utilize a linear or circular template. Amplification can be performed under any suitable temperature conditions, such as with thermal cycling or isothermally. Furthermore, amplification can be performed in an amplification mixture (or reagent mixture), which is any composition capable of amplifying a nucleic acid target, if any, in the mixture.

PCR amplification relies on repeated cycles of heating and cooling (i.e., thermal cycling) to achieve successive rounds of replication. PCR can be performed by thermal cycling between two or more temperature setpoints, such as a higher denaturation temperature and a lower annealing/extension temperature, or among three or more temperature setpoints, such as a higher denaturation temperature, a lower annealing temperature, and an intermediate extension temperature, among others. PCR can be performed with a thermostable polymerase, such as Taq DNA polymerase. PCR generally produces an exponential increase in the amount of a product amplicon over successive cycles.

As used herein an "amplicon" is a product of an amplification reaction. An amplicon can be single-stranded or double-stranded, or a combination thereof. An amplicon corresponds to any suitable segment or the entire length of a nucleic acid target.

As used herein, a primer is an oligonucleotide used for priming replication of a nucleic acid template. Thus, a primer is a shorter nucleic acid that is complementary to a longer template. During replication, the primer is extended, based on the template sequence, to produce a longer nucleic acid that is a complementary copy of the template. A primer may be DNA, RNA, or an analog thereof (i.e., an artificial nucleic acid), and may have any suitable length, such as at least about 10, 15, 20, 30 or 40 nucleotides. Primers are often synthesized chemically. Primers may be supplied as a pair of primers for amplification of a nucleic acid target. The pair of primers may be a sense primer and an antisense primer that collectively define the opposing ends (and thus the size) of a resulting amplicon.

As used herein, a "probe" is a nucleic acid used to detect and/or confirm the presence of another nucleic acid. A probe is typically connected to a detectable label. A probe may be a sequence-specific binding partner for a nucleic acid target and/or amplicon. An exemplary probe includes one or more nucleic acids connected to a dye (e.g. a fluorescent dye) or pair of dyes. The pair of dyes may respectively provide first and second emitters or an emitter (a reporter) and a quencher.

As used herein, a "label" is a distinguishing marker or identifier. It is typically connected to or incorporated into any entity, such as a molecule, molecular complex, compound, biological particle, or droplet. The label may be described as labeling the particular entity to produce a labeled entity. A label may, for example, be a dye that renders an entity optically detectable or at least more optically detectable. Exemplary dyes used for labeling are fluorescent dyes (fluorophores) and fluorescence quenchers.

As used herein, a "binding partner" or "ligand" is a member of an "interaction pair" of members that bind to one another. Each member may be an atom, molecule, molecular complex, compound, and/or biological particle (a cell, virus, organelle, or the like), among others. Binding partners may bind specifically to one another. Exemplary specific binding partners include biotin and avidin/streptavidin, a sense nucleic acid and a complementary antisense nucleic acid, a primer and its target, an antibody and a corresponding antigen, a receptor and its ligand, a nucleic acid and a protein that recognizes a sequence motif present in the nucleic acid, and the like.

As used herein, "particle" refers to discrete, small objects that may be in various shapes, such as a sphere (e.g. bead), capsule, polyhedron, and the like. Particles can be macroscopic or microscopic, such as microparticles or nanoparticles. Particles can be non-magnetic or magnetic. Magnetic particles may comprise a ferromagnetic substance, and the ferromagnetic substance may be Fe, Ni, Co, an iron oxide or the like.

BRIEF DESCRIPTION OF THE DRAWINGS

FIG. 6 illustrates recovery of 1 µm diameter Dynal MyOne Streptavidin coated beads using different filters. Control sample uses nylon net filter, all other samples are membrane filters with varying average pore diameters.

FIG. 7 illustrates recovery of 1 µm diameter Dynal MyOne Streptavidin coated beads at various stages of enrichment and using different length capture probes on enrichment beads (Spherotech cat. # SVP-150-4) using different filters. Control sample uses nylon net filter, all other samples are membrane filters with varying average pore diameters.

FIG. 8 shows enrichment using nylon net filters using either a manual protocol and vortexer or a completely automated protocol using a QIACube, commercially available from Qiagen.

FIG. 12 illustrates recovery of amplicon beads during two embodiments of an enrichment process—each using two different types of mixing: vortexer and QIAcube instrument.

FIG. 13 shows the enrichment efficiency (percentage of live beads measured) in the samples enriched using a vortexer and a QIAcube.

DESCRIPTION OF THE INVENTION

Figure 1:
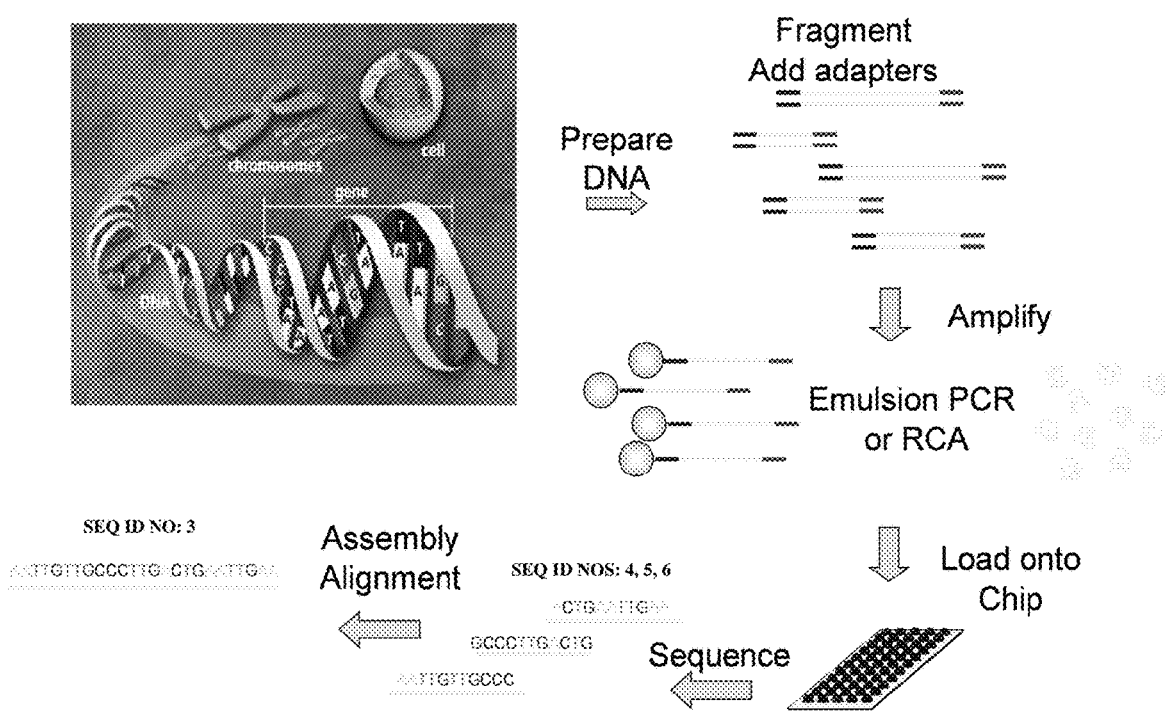
FIG. 1 shows one embodiment of a general workflow used in next generation sequencing approaches. DNA is fragmented and modified with adapters, prior to amplification in an emulsion.

Methods and compositions for enriching a population of particles containing an analyte are disclosed. In one embodiment, enrichment beads are used that are larger in size than the beads used for amplification. A separation device is employed that can retain larger beads with bound amplified beads. The technique finds many uses, including enriching for beads with clonally amplified template, which can be used in a variety of assays, including nucleic acid sequencing.

In one aspect of the invention, bead emulsion amplification is performed by attaching a nucleic acid template (e.g., DNA template) to be amplified to a solid support, preferably in the form of a generally spherical bead. The beads are suspended in aqueous reaction mixture and then encapsulated in a water-in-oil emulsion. In a preferred embodiment of the invention, at least one primer is bound to the bead and template DNA is included in solution in the amplification reaction mixture.

In certain embodiments, the emulsion is composed of discrete aqueous phase microdroplets, e.g., averaging approximately between 1 and 100 µm in diameter, enclosed by a thermostable oil phase. Each microdroplet contains, preferably, an amplification reaction solution (i.e., the reagents necessary for nucleic acid amplification). An example of an amplification reaction solution would be a PCR reaction mixture (polymerase, salts in buffer, dNTPs, etc.) and PCR primers (reverse and forward primers), with one primer attached to the bead. In some cases (because of limiting dilution), the template DNA is included in the reaction mixture. As a result, only a subset or portion of the microdroplet population includes the DNA bead and the template. This subset of the microdroplet population is the basis for the amplification. The remaining microcapsules or compartments do not contain template DNA and will not participate in amplification.

In a preferred embodiment, the nucleic acid template to be amplified by bead emulsion amplification is a population of DNA such as, for example, fragmented genomic DNA or cDNA. It is preferred that each member of the DNA population have a common nucleic acid sequence at the first end and a common nucleic acid sequence at a second end. This can be accomplished, for example, by ligating a first adaptor DNA sequence to one end and a second adaptor DNA sequence to a second end of each member of the DNA population. The nucleic acid template may be of any size amenable to in vitro amplification (including the preferred amplification techniques of PCR and asymmetric PCR). In a preferred embodiment, the template is between about 150 to 750 bp in size, such as, for example about 250 bp in size.

The beads used herein may be fabricated from any number of known materials. Example of such materials include: inorganics, natural polymers, and synthetic polymers. Specific examples of these materials include: cellulose, cellulose derivatives, acrylic resins, glass, silica gels, polystyrene, gelatin, polyvinyl pyrrolidone, co-polymers of vinyl and acrylamide, polystyrene, polyacrylamides, latex gels, dextran, rubber, silicon, plastics, nitrocellulose, natural sponges, silica gels, control pore glass, metals, cross-linked dextrans (e.g., Sephadex™), agarose gel (Sepharose™), and other solid phase supports known to those of skill in the art. In preferred embodiments, the emulsion beads are beads approximately 1 micron in diameter.

For use with the present invention, emulsion beads with or without attached nucleic acid template are suspended in a heat stable water-in-oil emulsion. It is contemplated that a portion of the microdroplet population include only one template and one bead. There may be many droplets that do not contain a template or which do not contain a bead. Likewise there may be droplets that contain more than one copy of a template. The emulsion may be formed according to any suitable method known in the art. One method of creating emulsion is described below but any method for making an emulsion may be used. These methods are known in the art and include adjuvant methods, counter-flow methods, cross-current methods, rotating drum methods, and membrane methods. Furthermore, the size of the microcapsules may be adjusted by varying the flow rate and speed of the components. For example, in dropwise addition, the size of the drops and the total time of delivery may be varied. Preferably, the emulsion contains a density of between about 10,000-1,000,000 beads encapsulated per microliter. This number depends on the size of the microspheres, droplets and the ratio of emulsion phases (i.e, oil to aqueous).

After encapsulation, the template nucleic acid may be amplified, while attached or unattached to beads, by any suitable method of amplification. In a preferred embodiment, DNA amplification is performed by PCR. PCR according to the present invention may be performed by encapsulating the nucleic acid template with a PCR solution comprising all the necessary reagents for PCR. Then, PCR may be accomplished by exposing the emulsion to any suitable thermocycling regimen known in the art.

Following amplification of the nucleic acid template and the attachment of amplification copies to the bead, the emulsion is "broken" (also referred to as "de-emulsification" in the art). There are many methods of breaking an emulsion. Processes for breaking emulsions known in the prior art include processes that use an inorganic or organic de-emulsifier, and processes that treat emulsions mechanically. One preferred method of breaking the emulsion uses additional oil to cause the emulsion to separate into two phases. The oil phase is then removed, and a suitable organic solvent is added. After mixing, the oil/organic solvent phase is removed. This step may be repeated several times. Finally, the aqueous layers above the beads are removed. The beads are then washed with a mixture of an organic solvent and annealing buffer (e.g., one suitable hybridization buffer or "annealing buffer" is described in the examples below), and then washed again in annealing buffer. Suitable organic solvents include alcohols such as methanol, ethanol, isopropanol and the like. In another embodiment the emulsion is broken by the addition of organic phase that solubilizes both aqueous phase and the oil/detergent and the homogenous solution removed after centrifugation or magnetic separation. The workup is usually then followed by washes with aqueous buffers, such as PBS with additional detergent (Tween-20).

As noted previously, high percentage of the beads may be negative if the goal is to minimize the number of beads that are associated with two or more different species of nucleic acid templates, i.e. minimize the instance where the beads comprise heterogeneous template. While the goal can be achieved, the results are inefficient. This inefficiency can be significantly ameliorated if beads containing amplicon (originating from the association with at least one template) are separated from those without amplicon (originating from beads with no associated template). An amplicon is defined as any nucleic acid molecules produced by an in vitro nucleic amplification technique. A separation step can be used to remove most or all of the beads with no DNA, leaving an enriched population of beads with one species of amplified DNA, i.e. most of the beads n the enriched population comprise homogeneous template.

The invention solves the low efficiency problem by selectively binding particles with DNA amplicons with enrichment beads (also called capture beads) and separating blank beads (i.e. beads lacking amplified template). One of the preferred embodiments is the use of enrichment beads that are larger in size than the beads used for amplification and a separation device (such as a filter) that can retain larger beads with bound amplified beads, allowing unbound beads to flow through. In one embodiment, the enrichment beads are modified to comprise capture oligos (also called capture probes) or a ligand, rendering them capable of binding only beads with DNA amplicons (also called "live" beads). After the initial separation is performed, the particles with amplicons are released from enrichment beads. For example, they can be released using the same separation device using a release solution that breaks the interaction between the amplified bead and enrichment bead. As a result, the beads carrying amplified DNA constitute the majority of the beads, and more preferably constitute 80-100% of the total beads population and serve as much better sample for DNA sequencing or other downstream analysis. The process can easily be automated. It is not intended that the process or compositions be limited to nucleic acid methods. The method and composition are generally applicable to any analyte.

DESCRIPTION OF PREFERRED EMBODIMENTS

As noted above, the enrichment techniques described herein find many uses, including enriching for beads with clonally amplified template, which can be used in a variety of assays, including nucleic acid sequencing. FIG. 1 schematically shows one embodiment of a general workflow used in next generation sequencing approaches. Emulsion PCR is used to clonally amplify template for subsequent sequencing.

Figure 2:
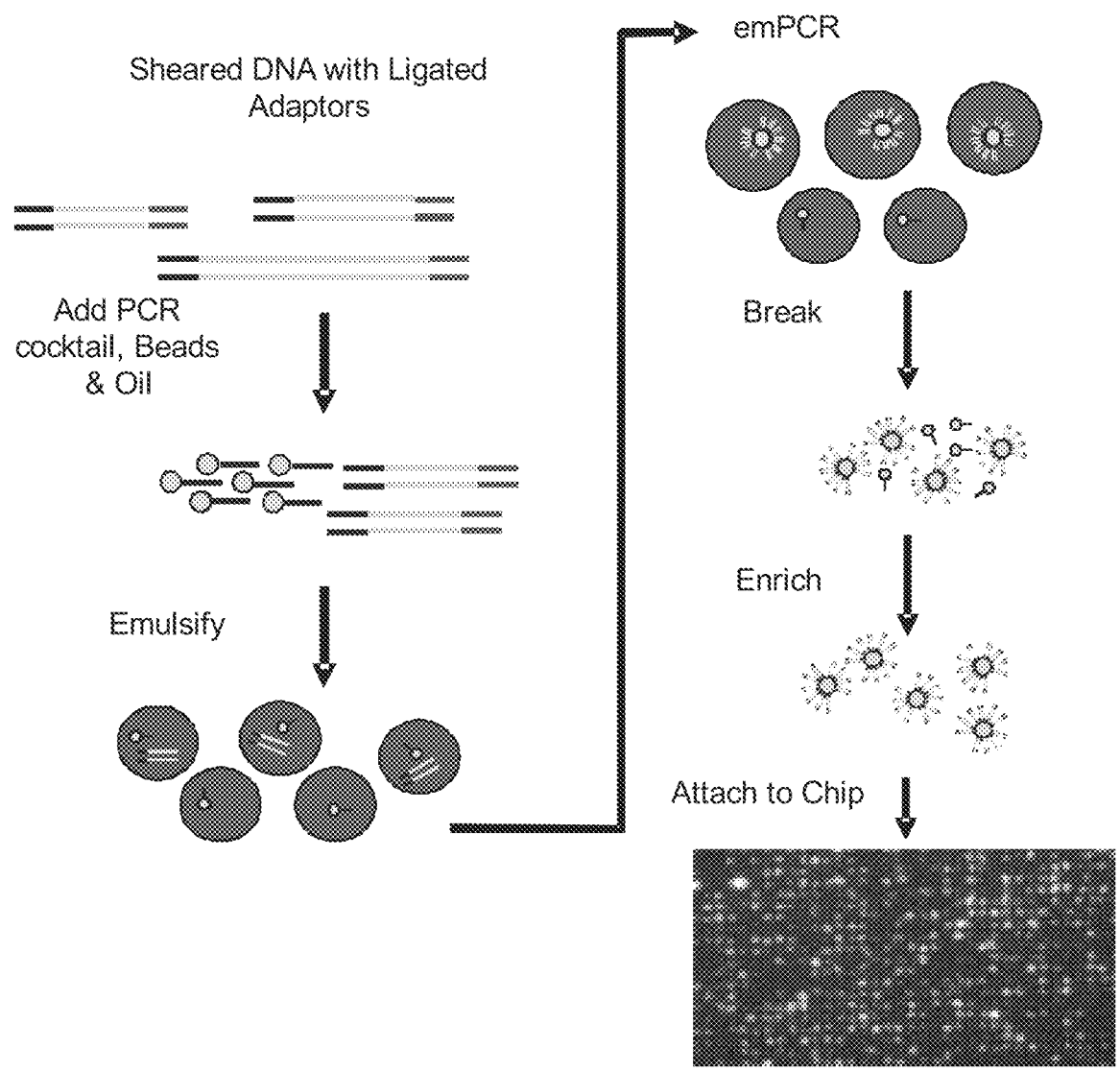
FIG. 2 shows one embodiment of a droplet amplification and enrichment scheme.

FIG. 2 is a schematic of one embodiment wherein the enrichment step is employed. After emulsion PCR, the emulsion is broken. The enrichment step generates a population of beads wherein the majority comprise amplicon. These beads are then loaded onto a chip and the template is subsequently sequenced.

Figure 3:
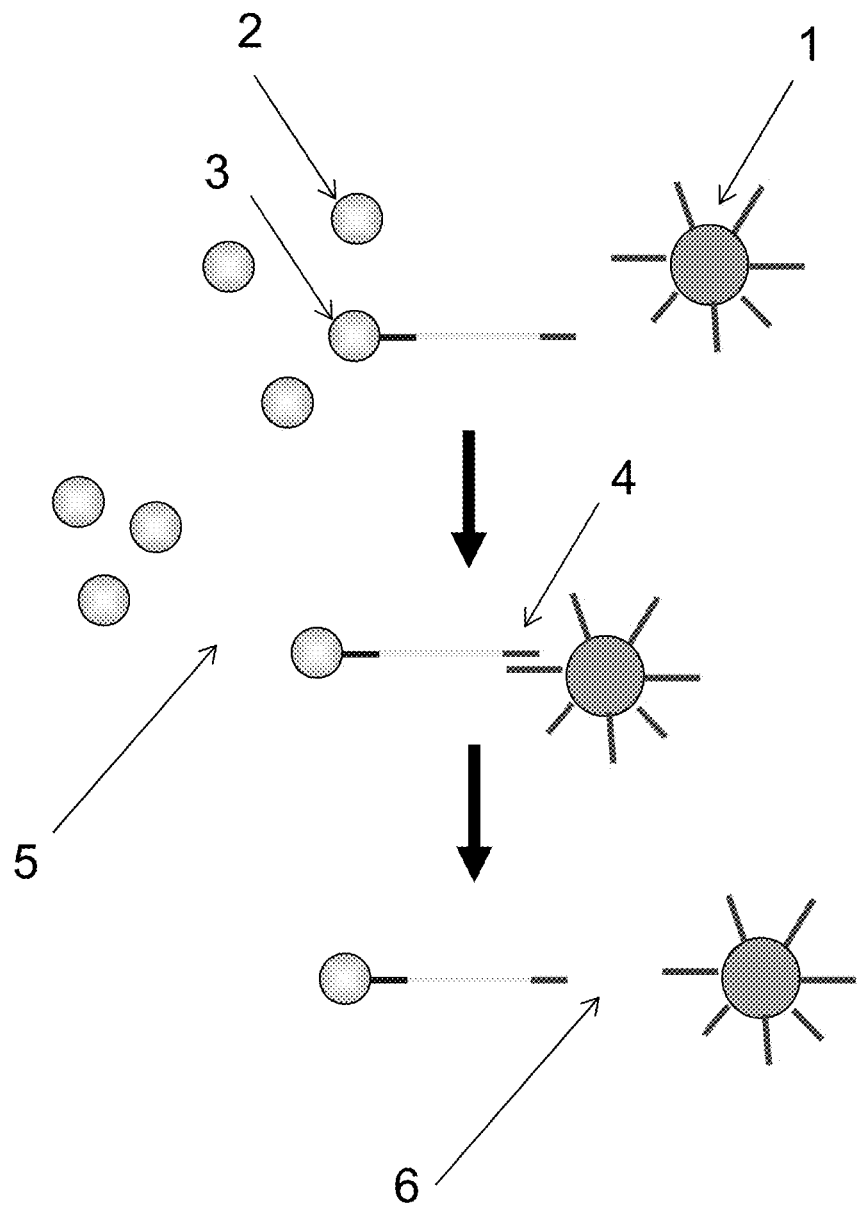
FIG. 3 depicts one embodiment of the enrichment process of the present invention, namely enrichment of microspheres/beads amplified in droplets. The elements/steps depicted as follows:
1. Enrichment Beads loaded with capture probes complementary to the amplicon
2. Beads without amplicons (blank)
3. Beads with amplicons
4. Beads with amplicon bound to the enrichment bead
5. Separation of enrichment beads with bound amplified beads from blank beads
6. Denaturation and separation of sequencing beads and enrichment beads
Figure 4:
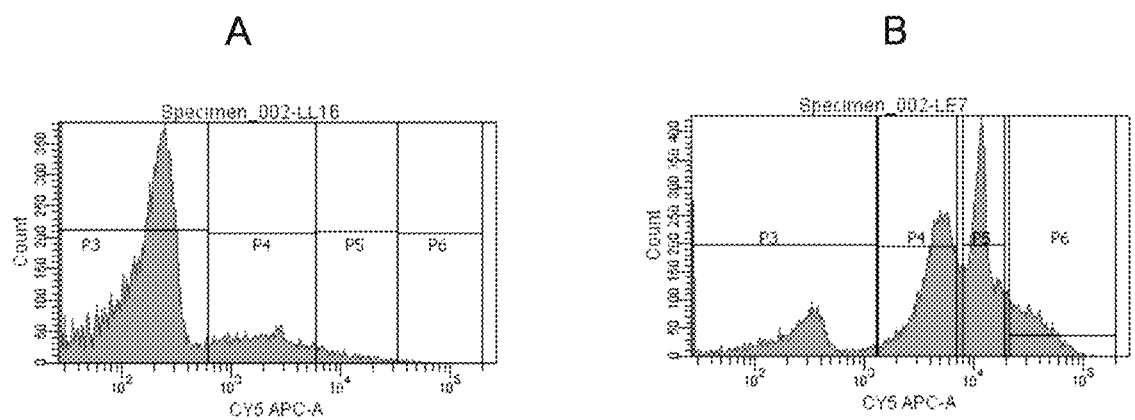
FIG. 4 shows signal distribution/histograms as measured by FACS for non-enriched (A) and enriched (B) particles. Particles containing amplified targets are visualized using fluorescently labeled (Cy5) oligonucleotide probe complementary to the distal end of the amplicon.

In one embodiment, the enrichment beads are modified to comprise capture oligos (also called capture probes) or a ligand, rendering them capable of binding only beads with DNA amplicons (also called "live" beads). FIG. 3 schematically shows the embodiment wherein capture oligos are used on the enrichment beads. These capture oligos hybridize with beads containing amplicon during enrichment. In one embodiment, the percentage of live can be measured by hybridizing a fluorescently labeled probe complementary to the distal end of the PCR amplicon. The labeled bead suspension can then be analyzed by using imaging techniques (fluorescent microscope) or Fluorescence Assisted Cell Sorting instrument (FACS). FIG. 4 shows a distribution of live beads before and after enrichment as measured using FACS.

In order to visualize emulsions and measure size distribution of emulsion droplets, imaging techniques (e.g. microscopy) or laser scattering methods (e.g. particle size analyzer, such as the commercially available Malvern MasterSizer) can be used. FIG. 5A shows microscope image of emulsion PCR with droplets containing beads while FIG. 5B shows droplets size distribution as measured by laser scattering instrument (MasterSizer).

In preferred embodiment the filter material comprises a single layer nylon mesh with narrow mesh size distribution. Using porous membranes with wide pore size distribution (despite the median pore size being the correct size) results in beads being entrapped in the pores and results in relatively poor recovery. FIG. 6 shows bead recovery percentage as a function of different filter materials. The control constitutes single layer of nylon mesh filter with mesh size of 10 μm. This sample also shows the best recovery.

FIG. 7 shows the workflow of amplified bead enrichment using capture probes of two different lengths. In one embodiment, the capture probe length is equivalent to the length of the adapter ligated to the DNA. In another embodiment the size of capture probe is shorter than the length of the adapter ligated to the DNA. As FIG. 7 shows the enrichment results (percentage live beads) is similar for both capture probes.

Several aspects of the performance of certain embodiments of the current invention can be measured. These include total bead recovery (i.e., number of beads at the start and at the end) and percentage live. Both factors impact the overall throughput. FIG. 8 illustrates the impact of using various enrichment methods on bead recovery and enrichment percentage by using various agitation mechanisms. In one embodiment, a vortexer is used to perform mixing operations and in another embodiment, repetitive pipetting is used by adapting QIACube, automated pipetting/centrifugation workstation. As seen in FIG. 8, the agitation method used has no significant impact on total beads recovery and percentage live.

Figure 9:
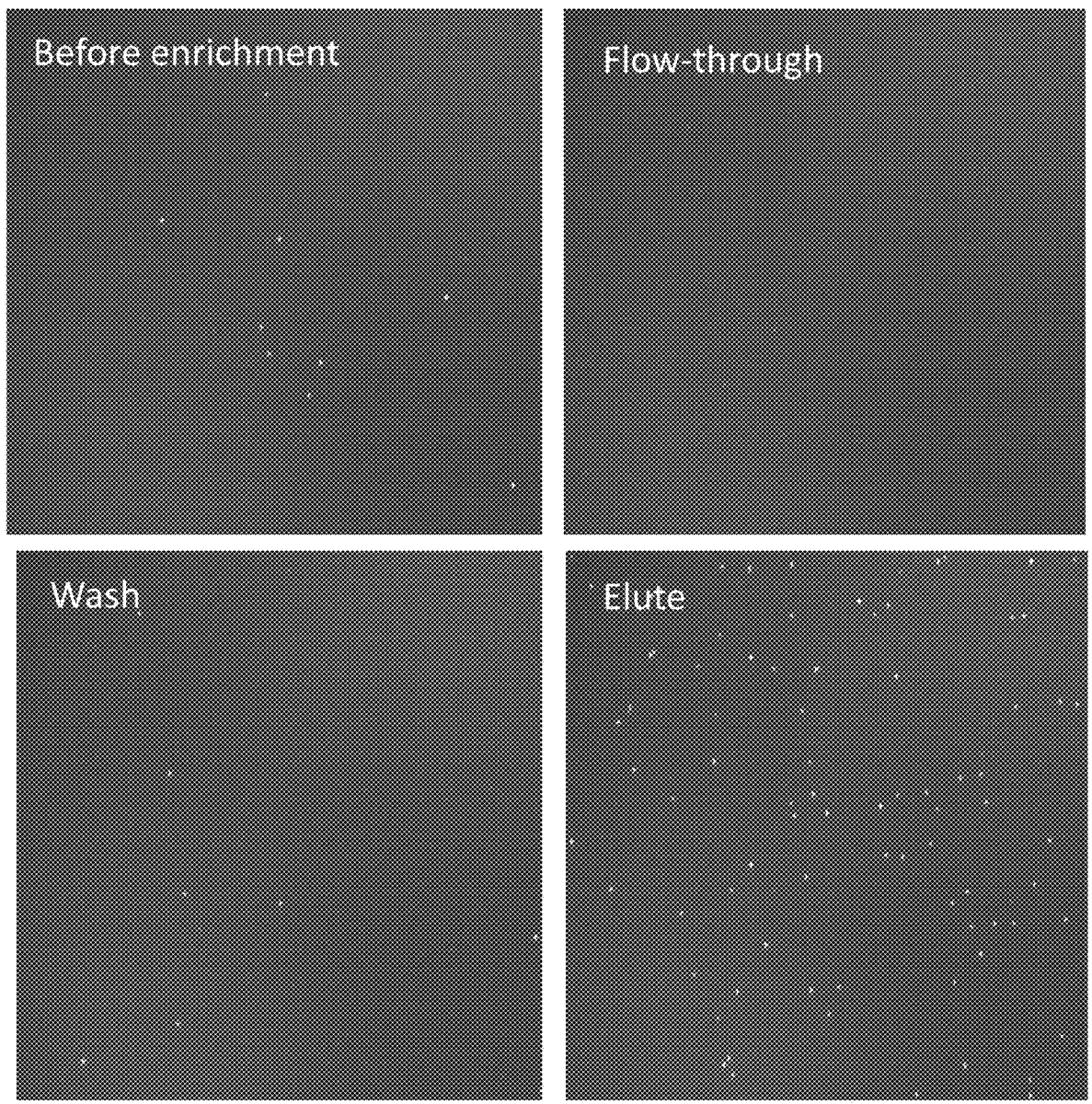
FIG. 9 shows images of the ePCR beads visualized by hybridizing Cy5 labeled probe complementary to the distal end of the amplicon and imaged using a Cellometer: Initial mixture, flowthrough, wash and elution using denaturing solution (sodium hydroxide).

In the practice of the present invention it is useful to perform live beads percentage assessment by way of hybridizing the beads with fluorescently labeled probe and imaging the beads on fluorescent microscope. In FIG. 9 images from fluorescent cell analysis instrument (Cellometer™) are shown. As can be seen in the images, the number of bright beads increases significantly after enrichment and can be also quantified using a combination of dark field and fluorescent imaging.

Figure 10:
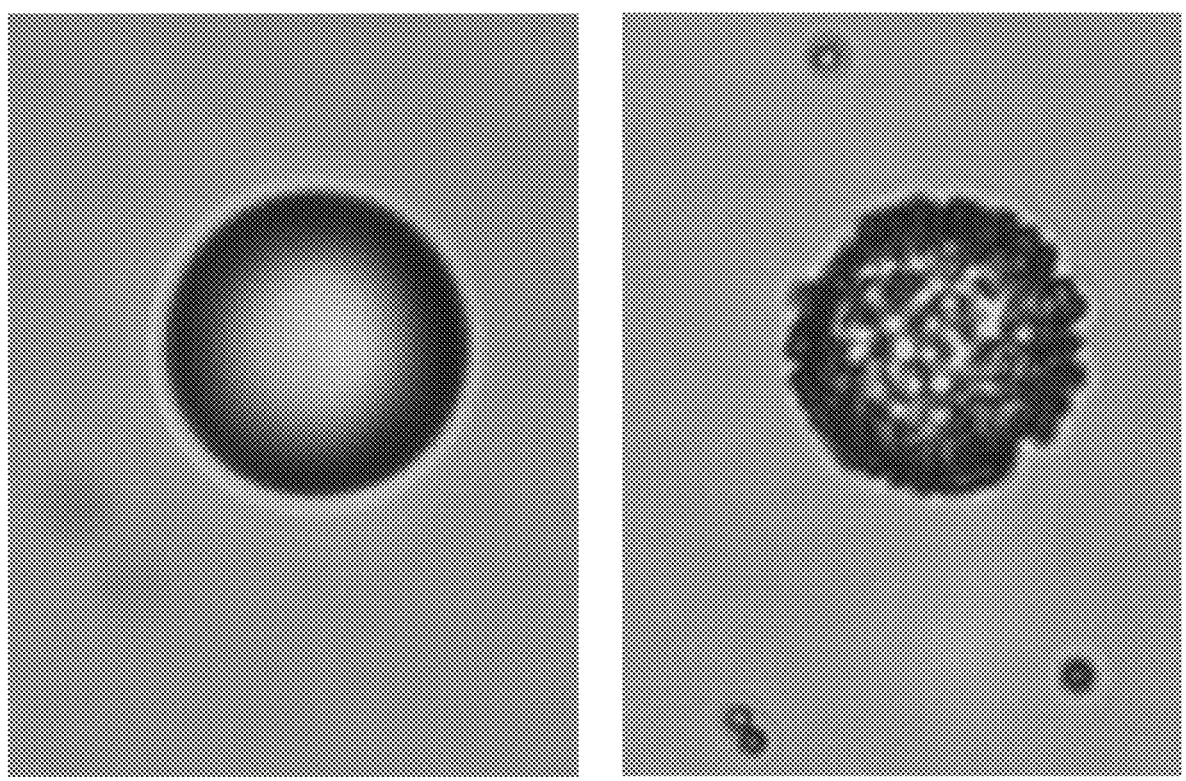
FIG. 10 shows microscope images of enrichment beads (16 µm, streptavidin coated, Spherotech) before and after binding to target ePCR beads. Target beads are visible bound to enrichment beads.

To visualize the process of binding of amplicon beads to enrichment beads a simple dark field microscopy can be used. FIG. 10 shows an example of such image, where the bead is imaged after incubation with blank beads and after binding amplicon beads. The amplicon beads are clearly visible as small objects attached to the enrichment bead, confirming specific capture.

Figure 11:
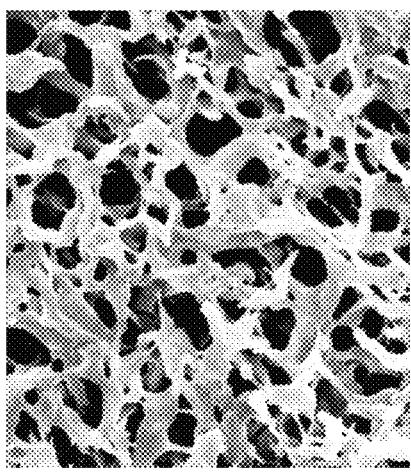
FIG. 11 shows microscope images of the membrane (left) and nylon net (right). Membrane has very wide range of pore size distributions while nylon net has very well defined openings.
Figure 11:
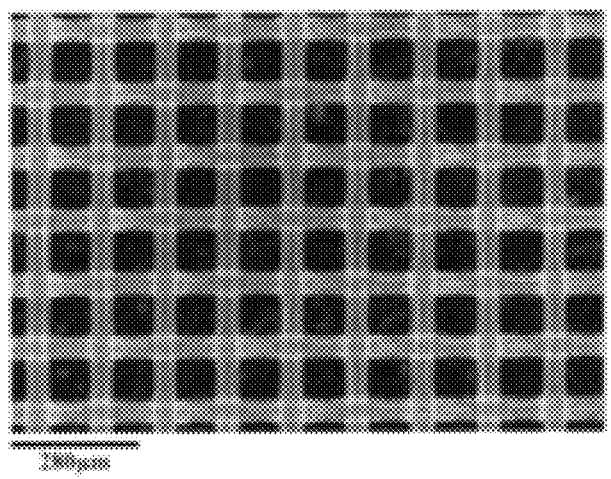

FIG. 11 illustrates microscopic images of two different types of filters: membrane and nylon net. As shown elsewhere in the specification, using nylon net mesh is a preferred embodiment as it results in much higher recovery of beads.

FIGS. 12 and 13 show measurements of beads at various stages of enrichment using either Vortexer of automated pipetting robot (QIACube) for performing enrichment (i.e., incubation of amplified beads with enrichment beads and maximizing collisions by either vortexing or repetitive pipetting. The speed of capture is achieved by maximizing collision events between amplicon beads and enrichment beads. This can be achieved by reducing volume or increasing collision rate (e.g, by increasing vortexing speed or pipetting rate).

EXPERIMENTAL

Example 1

Preparation of Emulsion PCR Samples and Emulsion PCR

This example describes a protocol for emulsion PCR using beads. The steps of the protocol are as follows:
1. Prepare the oil phase in one 50 ml tube. One ePCR reaction produces enough beads to populate 4 lanes of the MAX-Seq flowcell. All volumes are given in ml:

| Reagent | 1 Rxn | 2 Rxns | 3 Rxns | 4 Rxns |
|---|---|---|---|---|
| Tegosoft DEC (Evonik) | 4.4 | 8.8 | 13.2 | 17.6 |
| Mineral Oil | 1.2 | 2.4 | 3.6 | 4.8 |
| Surfactant (ABIL WE09)(Evonik) | 0.425 | 0.85 | 1.275 | 1.7 |

2. Vortex oil 10-20 seconds, until homogeneous. Set aside until step 4.
3. Prepare Aqueous Phase in 1.5 ml siliconized tube. All volumes are given in

| Reagent | 1 Rxn | Final Concentration | Mock |
|---|---|---|---|
| 10X PCR Buffer | 96 | 1X | 96 |
| 1M MgCl2 | 12.1 | 12.6 mM | 12.1 |
| dNTPs (25 mM each: 100 mM total) | 135 | 14 mM (total) | 0 |
| 2 mM B2_Primer_Unlabeled (reverse primer) | 6 | 12.5 μM | 0 |
| 10 μM M13F (forward primer) | 5 | 0.052 μM | 5 |
| 10 mg/ml BSA | 20 | 208 ng/μl | 20 |
| Template | Varies | | 0 |
| 10% Triton X-100 | 9.6 | 0.1% | 9.6 |
| Water | 515.3 | | 662.3 |

4. Transfer 5.5 ml emulsion oil to 50 ml tubes.
5. Finish preparing one* tube of aqueous phase by adding:
   a. 1.5 μl of Thermostable Inorganic Pyrophosphatase (2U/μl)
   b. 100 μl of e-grade Taq DNA polymerase to the aqueous phase and vortex.
   c. 60 μl of beads (2.68×10$^8$ beads total) and vortex.
6. Pipet aqueous phase to mix.
7. Place an IKA stirring tube with oil mix on the Ultra Turrax drive. Pierce the lid with a pipet tip.
8. Set the drive timer to 5 minutes and the speed to 6.
9. Add the aqueous phase to the oil phase using the peristaltic pump.
10. Insert pump tubing into 2 ml tube containing aqueous phase of emulsion. Turn pump on "forward" while the setting is on "purge". Watch the liquid being moved through the pump tubing until it reaches the outlet end of the tube. Change the setting to "slow" with the dial set to 5.
11. Start the Ultra Turrax drive.
12. Slowly dispense the complete aqueous volume into the oil phase while the stirrer is rotating.
13. After the aqueous phase is dispensed into the oil phase, continue stirring the mixture until the timer runs out for a total of 5 minutes.

Figure 5:
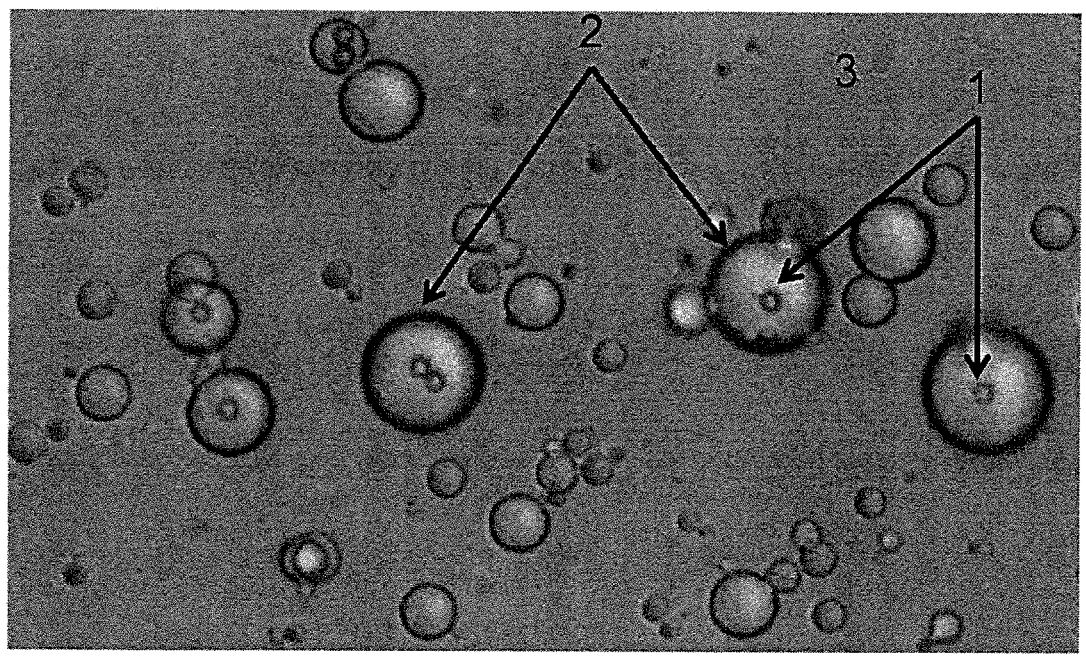
FIG. 5 shows (A) a microscope image of the beads/particles (1) inside emulsion droplets (2) on a background of bulk oil phase (3), and (B) droplets size distribution as measured by laser scattering instrument (MasterSizer).
Figure 5:
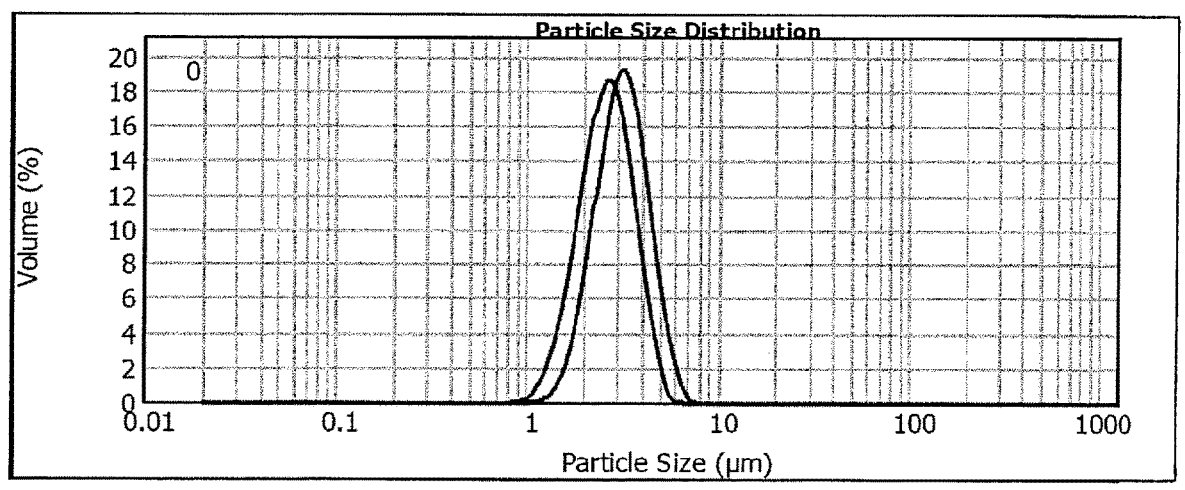

14. Set the repeat pipettor to 150 μl dispensing volume and use it to distribute the emulsion into the wells of a 96 well PCR plate (150 μl/well).
15. Seal the plate with an aluminum foil seal, and set aside the left over emulsion for imaging purposes on the microscope later.
16. Run protocol "E-PCR" on the thermocycler. Note which sample went into which cycler. The program will run for about 5 hours.
17. Return to step 5, as many times as is necessary to complete all emulsions.
18. Pipet 5 μl of leftover emulsion onto a glass microscope slide, and place a coverslip over it. Observe under the microscope. Micro-compartments containing (on average) one bead should be apparent. Very few beads should be observed in the oil phase. FIG. 5 shows the microscope image of beads inside emulsion droplets.
19. Pipet entire aqueous phase (960 μl) into the 50 ml tube containing the oil phase.
20. Mix on the Talboys digital vortexer for 2 minutes and 15 seconds at speed 2200 rpms.
21. Using a repeating pipette, load 50 μl/well of the emulsion into a 96 well plate. Seal with an aluminum foil seal, and set aside the left over emulsion for imaging purposes on the microscope later.
22. Run protocol "EPCR-1"" on the thermocycler. Note which sample went into which cycler. The program will run for about 6 hours.
23. Return to step 5, as many times as is necessary to complete all emulsions. Pipet 5 μl of leftover emulsion onto a glass microscope slide, and place a coverslip over it. Observe under the microscope. Micro-compartments containing (on average) one bead should be apparent. Very few beads should be observed in the oil phase.

PCR Cycling Parameters, EPCR-1
1. 95° C. for 3 minutes
2. 94° C. for 15 seconds
3. 57° C. for 30 seconds
4. 70° C. for 30 seconds
5. Go To Step 2, 119 Times
6. 72° C. for 2 minutes
7. 2° C. forever Example 2

Emulsion PCR Processing

This example describes a protocol for breaking the emulsion and recovering the beads. The steps of the protocol are as follows:
1. Pool each emulsion into a 50 ml conical tube using a blunt needle fitted with a 10 ml syringe with rubber plunger.
2. Add isopropanol to 20 ml mark.
3. Vortex on Talboys Vortexer, for 45 seconds at 3000 rpm. No clumps should remain.
4. Centrifuge in the tabletop centrifuge at 6000 RPM for 2 minutes.
5. Decant supernatant.
6. Repeat steps 2-4. After centrifugation, set the tube on a magnet rack and carefully remove the supernatant with a 10 ml serological pipette. Avoid removing beads.
7. Use a P200 pipette to remove any residual isopropanol from the bottom of the tube while the tube sits on a magnet rack.
8. Add NXS buffer (10 mM Tris-HCl, 100 mM NaCl, 1% SDS, 1% Triton X-100, pH=8.0) to 20 ml mark.
9. Vortex on Talboys Vortexer for 90 seconds, at 3000 RPM.
10. Centrifuge in the tabletop centrifuge for 3 minutes at 6000 RPM.
11. Decant the supernatant. If the pellet comes off the tube wall, set the tube on a magnet and carefully remove all of the supernatant by pipetting with a 10 ml serological pipet.
12. Resuspend beads in 500 μl TE buffer and transfer to a 1.5 ml siliconized tube.
13. Set the tube on the magnet for 1 minute, and remove/discard supernatant.
14. Wash 3 times with 500 μl TE buffer (vortex, then spin for 1 second in a mini-centrifuge, set the tube on a magnet for 30 seconds, then pipet off and discard the supernatant).
15. Add 500 μl of 0.1 N NaOH, mix well by pipetting and incubate for 5 minutes. The 0.1 N NaOH should be diluted fresh from a 10N stock.
16. Set tube on magnet for 30 seconds, then aspirate and discard NaOH.
17. Wash with 500 μl 0.1 N NaOH, by adding solution, vortexing, briefly spinning down, then setting on the magnet until solution clears, and aspirating/discarding supernatant.
18. Wash three times with 500 μl 1× hybridization buffer (100 mM Tris-HCl, 1M NaCl, 0.2% Tween-20, pH=8.0).

Example 3

Enrichment Using Glycerol Density Centrifugation

This example describes a protocol for one embodiment of an enrichment protocol, utilizing density centrifugation.

Materials and Equipment Required:
  Enrichment Beads: 3.2 μm polystyrene beads coated with streptavidin, Spherotech part # SVP 30-5

```
Oligonucleotide
                                               (SEQ ID NO: 1)
Bis biotin 5' TTTTTTTTTACTTCAATTTACTATGTAGCAAAGG
3')
```

Timer
  1 ml, 200 μl, 20 μl and 10 μl pipettes and matching tips
  Eppendorf centrifuge 5424 or equivalent
  Glycerol
  B&W buffer
  Nuclease free water
  TE buffer
  Hybridization buffer
  1.5 ml Eppendorf tubes
  Thermocycler
  Vortexer Procedure:
  1. Bind primer to Enrichment beads:
    a. Pipet an aliquot of 540 μl beads into a 1.5 ml Eppendorf tube.
    b. Wash 3 times with 1 ml 1× B&W buffer (5 mM Tris-HCl, 0.5 mM EDTA-Na, 1M NaCl, pH=8.0):
      i. Add 1 ml B&W buffer
      ii. Pipet to mix
      iii. Spin in benchtop centrifuge for 1 min. at 15,000 RPM
      iv. Pipet off and discard supernatant c. Add 540 µl of 25 µM Bisbiotin_B2 in B&W buffer
d. Pipet to mix
e. Incubate on tube rotator for one hour at room temperature
f. Repeat step 1b
g. Resuspend in 60 µl B&W buffer and store at +4° C. for up to one week
2. Prepare Magnetic beads to be enriched:
   a. Obtain beads with single stranded DNA resulting from a full-scale or half-scale emPCR performed with a limited amount of template DNA and B2_Primer.
   b. Resuspend these beads in the following volume of TE Buffer:
      i. Half-Scale: 20 µL
      ii. Full Scale: 40 µL
3. Bind Magnetic beads to Enrichment beads:
   a. In a 0.2 ml PCR tube, combine an equal volume of Magnetic beads and Enrichment (for example, to enrich all of a half-scale emPCR, use 20 µL Enrichment beads).
   b. Pipet to mix
   c. Incubate at 58° C. in the thermocycler for 1 hour. Pipet gently every 10 minutes.
   d. Remove tube from cycler and allow it to come to room temperature (about 5 minutes on benchtop)
4. Freshly prepare glycerol dilutions:
   a. Using a 1 ml syringe to transfer the appropriate amount of 100% glycerol (see table below) to a 1.5 ml Eppendorf tube, and fill with nuclease-free water to 1 ml.
   b. Vortex well

|  | 1 µm magnetic beads | 3 µm magnetic beads |
| --- | --- | --- |
| % glycerol | 60 | 80 |
| ml glycerol in 1 mL | 0.6 | 0.8 |
| rpm | 13,000 | 15,000 |
| rcf | 15,871 | 21,130 |

5. Separate the beads into two fractions ("live" and "null"):
   a. Pipet 300 µl diluted glycerol into the bottom of a 1.5 ml Eppendorf tube
   b. Pipet the bead mixture from step 3d onto the top of the glycerol—the aqueous bead mixture should "float" atop the glycerol.
   c. Spin in a benchtop centrifuge for 1 minute at the speed indicated in the table above.
   d. Two distinct populations of beads should be present:
      i. A dense pellet of null Magnetic beads at the bottom of the tube
      ii. A tan-colored layer of live Magnetic beads mixed with Enrichment beads atop the glycerol
   e. Pipet off the top layer and save these beads in a 1.5 mL siliconized tube.
      (Optional: save and measure live beads using fluorescent probe to determine no live beads were lost to the pellet).
6. Denature the DNA to separate the Enrichment beads from the Magnetic beads:
   a. Wash the beads 3 times with 1 mL TE buffer:
      i. Add 1 mL TE buffer
      ii. Pipet to mix
      iii. Set on magnet until the supernatant is no longer tan (about 5 minutes)
      iv. Pipet off and discard supernatant (this will likely be very "cloudy" in appearance, due to the excess Enrichment beads)
   b. Re-suspend the beads in 1 mL of 0.1 N NaOH
   c. Pipet to mix
   d. Incubate for 3 min at room temperature
   e. Set on magnet until solution clears, then pipet off and discard the supernatant
   f. Wash twice with 0.1 N NaOH
   g. Wash with 3 times with 1 ml of 1× Hybridization buffer (as described in steps 6.a.i-iv) until the supernatant is clear.
   h. Proceed to hybridize with appropriate primer for sequencing Example 4

Enrichment Using Filter Method (Syringe Filter)

This example provides a protocol for enrichment using a filter method. The enrichment beads are bound to the emulsion beads to form a complex. The complex is trapped or captured on the filter and a combination of two syringes and gravity is used to achieve the separation. In this embodiment capture probe is bound to enrichment beads first.

Materials and Equipment Required:
   Nylon net syringe filters, Millipore, 25 mm diameter, 11 µm pore size, part # NY1102500
   16 µm streptavidin coated polystyrene beads, Spherotech, part # SVP-150-4.
   Whatman Swin-Lok Filter Holder 420200-25 mm
   5 ml disposable syringes

```
Bisbiotinylated oligonucleotide B2
                                            (SEQ ID NO: 1)
(Bis biotin 5' TTTTTTTTTTACTTCAATTTACTATGTAGCAAAGG
3')
```

Timer
   1 ml, 200 µl and 10 µl pipettes and matching tips
   Eppendorf centrifuge 5424 or equivalent
   B&W buffer
   Nuclease free water
   TE buffer
   Hybridization buffer
   1.5 ml Eppendorf tubes
   Thermocycler
   Vortexer
   Enrichment Buffer:

| Component | ml | final conc. |
| --- | --- | --- |
| 10 x PBS | 1 | 1 x |
| 5% BSA | 0.4 | 0.20% |
| 10 mg/ml salmon sperm DNA | 0.1 | 0.1 mg/ml |
| 25% Tween 20 | 0.02 | 0.05% |
| nuclease free water | 8.46 |  |
| 5% sodium azide | 0.02 | 0.01% |
| total volume | 10 |  |

Procedure:
   1. Bind capture oligo to Enrichment beads
      a. Pipet an aliquot of 540 µl beads into a 1.5 ml Eppendorf tube.

b. Wash 3 times with 1 ml 1× B&W buffer:
   i. Add 1ml B&W buffer
   ii. Pipet to mix
   iii. Spin in benchtop centrifuge for 1 min. at 15,000 RPM
   iv. Pipet off and discard supernatant
c. Add 540 µl of 25 µM Bisbiotin_B2 in B&W buffer
d. Pipet to mix
e. Incubate on tube rotator for one hour at room temperature
f. Repeat step 1b
g. Resuspend in 60 µl B&W buffer and store at +4° C. for up to one week.

2. Prepare Magnetic beads to be enriched:
   a. Obtain beads with single stranded DNA resulting from a full-scale or half-scale emPCR performed with a limited amount of template DNA and B2_Primer.
   b. Resuspend these beads in the following volume of TE Buffer:
      i. Half-Scale: 20 µL
      ii. Full Scale: 40 µL 3. Bind Magnetic beads to Enrichment beads:
   a. Wash 5.7 ml STV spherotech beads 2 times with enrichment buffer and re-suspend in 5.7 ml enrichment buffer.
   b. Dispense STV spherotech beads in a 1.5 ml tube. Separate on a magnet and remove liquid. Resuspend beads in 400 ul of enrichment buffer.
   c. Add emPCR beads mix to the enrichment beads. Use 150 ul of enrichment buffer to rinse the tube and add this rinse to the spherotech beads.
   d. Incubate on rotating shaker at RT for 4 hours at speed 2.

4. Separate the beads into two fractions ("live" and "null"):
   a. Dilute each sample to 1ml with 1×PBS.
   b. Place filter disc in filter holder and attach syringe barrel to the filter holder.
   c. Filter diluted sample through filter by placing it in the syringe barrel. Save the filtrate for measurement of unbound (blank) beads (Add 2×1 ml PBS and add to filter, discard the filtrate
   d. Fill a new syringe with 3 ml PBS and attach it to the opposite end of the filter holder.
   e. Gently press the buffer up through the filter and into the syringe barrel.
   f. Remove bottom syringe and the solution will free run through the filter and discard the solution.
   g. Fill a new syringe with 3 ml 0.1N NaOH and attach it to the opposite end of the filter holder.
   h. Gently press the buffer up through the filter and into the syringe barrel.
   i. Incubate at RT for 2 minutes
   j. Remove bottom syringe and the solution will free run through the filter.
   k. Collect this solution in a 15 ml tube (filtrate A) containing Live beads.
   l. Fill a new syringe with 3 ml 0.1N NaOH and attach it to the opposite end of the filter holder.
   m. Gently press the buffer up through the filter and into the syringe barrel.
   n. Incubate at RT 1 minutes
   o. Remove bottom syringe and the solution will free run through the filter.
   p. Collect this solution in a 15 ml tube (filtrate B) containing Live beads.
   q. Combine filtrate A and B.
   r. Wash with 3 times with 1 ml of 1× Hybridization buffer Example 5

Enrichment Using Nylon Net Spin Filters

This example describes an embodiment of enrichment employing filters and centrifugation. In this embodiment a reverse ePCR primer which is biotinylated is used.

This eliminates the need to bind capture probe to the enrichment beads.

After the initial separation is performed, the particles with amplicons are released from enrichment beads. In this example, they are released using the same separation device (e.g. spin filter) using a release solution that breaks the interaction between the amplified bead and enrichment bead. In this example, the spin filter with the emulsion beads attached to the captured enrichment beads is moved to a new tube (e.g. spin column). After the release solution is applied, the tube is centrifuged and the beads with amplicons are eluted and go to the bottom of the tube. The enrichment beads remain trapped in the filter. The beads with amplicons are collected and the filter with the trapped enrichment beads is discarded.

Preparation of Capture Beads
1. Vortex bottle with capture beads (SuperAvidin™ coated polystyrene beads, mean diameter 15.3 µm, Bangs Laboratories) to re-suspend the beads.
2. Transfer 400 ul capture beads to a 1.5 ml centrifuge tube and spin down at 15,000 rpm for 1 min
3. Remove supernatant and re-suspend beads in 1 ml enrichment buffer.
4. Spin beads down at 8000 rpm for 1 min and remove as much supernatant as possible without losing beads. Leave~50 ul liquid behind.
5. Repeat steps 3 and 4.
6. Re-suspend beads in 100 ul enrichment buffer.

Enrichment
1. Wash beads after recovery from emulsion with enrichment buffer, place tube with beads on a magnet stand to remove the supernatant.
2. Re-suspend beads in 50 ul enrichment buffer.
3. Mix capture beads and Dynal beads in a 2 ml tube and place the tube in the shaker on the QiaCube.
4. Set the shaker at 900 rpm for 15 minutes.
5. Place spin filter with nylon mesh membrane in a 2 ml tube (spin column).
6. Transfer bead mixture to spin filter and spin for 1 minute at 8000 rpm. Most of the null beads are removed in this step.
7. Transfer spin filter to a new 2 ml tube and add 300 ul PBS/0.05% Tween 20
8. Spin for 1 minute at 8000 rpm.
9. Add 300 ul PBS/0.05% Tween 20 to the spin filter and spin for 1 minute at 8000 rpm.
10. Transfer spin filter to a fresh 2 ml tube.
11. Add 300 ul 0.2 N NaOH and let stand for 5 minutes.
12. Spin for 1 minute at 8000 rpm.
13. Repeat steps 11 and 12.
14. Discard the spin filter and place the 2 ml tube with eluted beads on a magnet rack.
15. Remove the supernatant and re-suspend the beads in PBS/0.05% Tween 20.
16. Repeat step 15 twice for a total of 3 washes.
17. Re-suspend live beads in 20 ul PBS.

| Enrichment buffer | | |
| --- | --- | --- |
| Component | ml | final conc. |
| 10× PBS | 1 | 1× |
| 5% BSA | 0.4 | 0.20% |
| 10 mg/ml salmon sperm DNA | 0.1 | 0.1 mg/ml |
| 25% Tween 20 | 0.02 | 0.05% |
| nuclease free water | 8.46 | |
| 5% sodium azide | 0.02 | 0.01% |
| total volume | 10 | |

Example 6

Measurement of Beads and Amplicons

This example examines the resulting beads by light scattering assay and the resulting amplicons by fluorescence.

Beads Sample Preparation

Starting Material: Beads with double-stranded, labeled DNA, in 1× Hybridization buffer.

1. Dilute NEBuffer 2 (New England Biolabs, cat. # B7002S; 50 mM NaCl, 10 mM Tris-HCl, 10 mM $MgCl_2$, 1 mM DTT pH 7.9@25° C.) to 1× concentration. You will need 2.2 ml for the standard curve, and 120 μl per sample. Spin down the beads and remove as much buffer as possible, leaving behind only beads.
2. Add to the beads 49 μl 1× NEBuffer 2.
3. Add to the beads 1 μl Exonuclease III (Enzymatics, cat. # X8020L).
4. Incubate at 37° C. for a total of 60 minutes, mixing the samples to resuspend the beads by either vortexing gently, or pipetting half-way through the incubation. (During the second half of this incubation, you may begin preparing samples for a standard curve).
5. Add 70 μl of 1× NEBuffer 2 to each sample and vortex well. Spin sample down to pellet beads (or set on magnet), then proceed to "Loading the TECAN Plate".

Standard Curve Preparation

Starting Material: 250 nM stock of the Cy5-labeled probe (5'Cy5-ACT TCA ATT TAC TAT GTA GCA AAG G 3') (SEQ ID NO: 2) used for probing the beads (this can be achieved by adding 1 μl of 250 μM stock into 1 ml of 1× NEBuffer 2).

1. Dilute samples according to the following table:

| Concentration [nM] | Picomoles | 250 nM DNA (μl) | NEBuffer 2 [μl] |
| --- | --- | --- | --- |
| 200 | 40 | 160.0 | 40.0 |
| 100 | 20 | 80.0 | 120.0 |
| 50 | 10 | 40.0 | 160.0 |
| 25 | 5 | 20.0 | 180.0 |
| 12.5 | 2.5 | 10.0 | 190.0 |
| 6.25 | 1.25 | 5.0 | 195.0 |
| 3.125 | 0.625 | 2.5 | 197.5 |

Loading the TECAN Plate

Starting Material: Experimental and Standard Curve samples, and black 96-well flat bottomed Corning plate.

1. Load 100 μl each sample into the plate. Note which samples you load into each well.
2. Load one well with only 1× NEBuffer 2 (this serves as a blank).

Running the Tecan Instrument

1. Open Magellan 6 from the desktop.
2. Click "move plate out" button. This will cause the door to open on the instrument.
3. Load the plate with well A1 in the top, left-hand corner.
4. Click "move plate in" button. This will cause the plate to be sucked into the instrument.
5. Press "go" button.
6. Select "Raw Data", click "go"
7. Chose which wells you would like measured (all yellow wells will be measured).
8. Drag "Fluorescent Intensity" under the plate diagram.
9. If using Cy5: Choose the following options: Select filter 640 for red.
10. Mode: Top.
11. Lag: 0.
12. Int. Time: 20.
13. Read flashes: 25.
14. Gain: Optimal. (If the samples read much lower or higher than the standard curve samples, then this may need to be altered, or samples diluted).
15. Press "go," and readings will be taken.
16. A plate diagram will come up with data in it. To save the data, click "edit" then "copy to excel." This will open excel and insert the data. Copy and paste the additional details about the run into the excel sheet for record keeping.

Light Scattering Assay

1. Remove all supernatant from bead sample, and resuspend beads in 100 μl of 1× Thermol Pol Buffer.
2. Add 50 μl of these beads into 450 μl 1× ThermoPol Buffer (New England Biolabs, cat. # B9005S; 20 mM Tris-HCl, 10 mM $(NH_4)_2SO_4$, 10 mM KCl, 0.1% Triton® X-100, pH 8.8@25° C. in a cuvette.
3. Pipet to mix.
4. Determine absorbance at 600 nm on the spectrophotometer.
5. Calculate relative amplicon load using fluorescent signal and bead count.

Example 7

Enrichment Using Streptavidin Coated Glass Slide/Plate

Standard ePCR reaction was performed and beads were recovered, then resuspended in enrichment buffer. The beads suspension was then deposited onto the slide surface and incubated at RT for 2 hours. The supernatant was then removed (non-bound beads) and the slide surface was washed with 1×PBST. The slide was then exposed to 0.1 N NaOH solution and incubated for 2 minutes to release enriched beads. The liquid was removed and additional wash with 0.1 N NaOH was performed. The beads suspension was then placed on magnetic separator and supernatant removed. The beads were washed with 2× PBST and absorption was measured at 600 nm to determine beads concentration. The beads were then hybridized with fluorescently labeled probe to determine % enrichment and compare with initial % live beads. The enrichment in this case showed initial % live to be 17% (before enrichment) and 30% (after enrichment).

The invention claimed is:

1. A method of enriching, comprising:
   a) providing
      i) an emulsion comprising one or more aqueous compartments in oil, at least some of said compartments comprising PCR reagents, a first PCR primer immobilized on an emulsion bead, a second biotinylated PCR primer in solution, and a nucleotide sequence template; and
      ii) enrichment beads, wherein said enrichment beads are larger than emulsion beads in said compartments;
   b) exposing said emulsion to conditions so as to amplify at least some of said template to produce amplified template on at least some of said emulsion beads in at least some of said compartments, wherein one strand of said amplified template terminates with biotin; and
   c) enriching for emulsion beads comprising said amplified template by contacting said emulsion beads with said enrichment beads, wherein said emulsion beads comprising said amplified template bind to said enrichment beads so as to make a population of emulsion bead—enrichment bead complexes; and
   d) capturing at least some of said population of complexes under conditions such that a majority of said emulsion beads not comprising amplified template are not captured.

2. The method of claim 1, further comprising, after step d):
   e) subjecting said population of complexes to conditions so as to separate said emulsion beads comprising amplified template from said enrichment beads such that the majority of said emulsion beads comprising amplified template separate from said enrichment beads.

3. The method of claim 2, wherein said emulsion beads comprising amplified template are separated from said enrichment beads by centrifugation.

4. The method of claim 2, wherein said conditions of step e) comprise denaturing conditions.

5. The method of claim 2, wherein said emulsion beads separated from said enrichment beads are magnetic.

6. The method of claim 5, wherein said emulsion beads separated from said enrichment beads are exposed to a magnet.

7. The method of claim 2, further comprising recovering said separated emulsion beads comprising amplified template so as to create an enriched population contaminated with less than 10% of beads without amplified template.

8. The method of claim 7, wherein said enriched population is contaminated with less than 1% of beads without amplified template.

9. The method of claim 7, wherein said enriched population comprises between 1 and 20 million beads.

10. The method of claim 1, wherein each compartment comprises on average less than one template.

11. The method of claim 1, further comprising breaking said emulsion after step b) and before step c).

12. The method of claim 1, wherein said enrichment beads comprise streptavidin.

13. The method of claim 1, wherein the capturing in step d) comprises size selection.

14. The method of claim 13, wherein said size selection comprises density centrifugation.

15. The method of claim 13, wherein said size selection comprises capturing at least some of said population of complexes on a surface.

16. The method of claim 15, wherein said surface comprises the surface of a filter.

17. The method of claim 16, wherein said filter is a single layer nylon mesh.

18. The method of claim 16, wherein said filter is positioned in a spin column.

19. The method of claim 18, wherein said spin column is centrifuged during step d) so as to facilitate passage of said uncaptured emulsion beads through said filter.

20. The method of claim 1, wherein at least a portion of said enrichment beads binds more than one of said emulsion beads comprising amplified template.

21. The method of claim 1, wherein said PCR reagents comprise a polymerase and nucleotides or nucleotide analogues in a buffer.

22. The method of claim 1, wherein said template comprises sheared DNA fragments.

23. The method of claim 22, wherein said sheared DNA fragments comprise 3' and 5' adaptors.

24. The method of claim 23, wherein said first PCR primer and said second PCR primer are complementary to a portion of one of said adaptors.

25. The method of claim 1, wherein said exposing to conditions of step b) comprises temperature cycling.

26. The method of claim 1, wherein said emulsion beads in said compartments are magnetic and said magnetic beads are recovered after step b), and thereafter exposed to a magnet, and washed.

27. The method of claim 1, wherein said emulsion beads are 1 μm in diameter and said enrichment beads are approximately 15 μm in diameter.

* * * * *